(12) United States Patent
Sundar et al.

(10) Patent No.: US 9,727,697 B1
(45) Date of Patent: Aug. 8, 2017

(54) SYSTEM AND APPROACH FOR INTEGRATION OF PARAMETERS FROM WEARABLE CLOUD CONNECTED ACCESS CONTROL DEVICES

(71) Applicant: Honeywell International Inc., Morris Plains, NJ (US)

(72) Inventors: Naga Sundar, Madurai (IN); Jenifram Ponraman, Natham (IN); MuthuKumar Azhagesan, Tuticorin (IN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/133,014

(22) Filed: Apr. 19, 2016

(51) Int. Cl.
| | |
|---|---|
| *G06F 19/00* | (2011.01) |
| *A61B 5/00* | (2006.01) |
| *A61B 5/0205* | (2006.01) |
| *A61B 5/024* | (2006.01) |
| *A61B 5/021* | (2006.01) |
| *A61B 5/1455* | (2006.01) |
| *G08B 25/00* | (2006.01) |
| *G07C 9/00* | (2006.01) |
| *H04L 29/08* | (2006.01) |
| *G08B 21/04* | (2006.01) |

(52) U.S. Cl.
CPC .......... *G06F 19/3418* (2013.01); *A61B 5/002* (2013.01); *A61B 5/021* (2013.01); *A61B 5/024* (2013.01); *A61B 5/02055* (2013.01); *A61B 5/14551* (2013.01); *A61B 5/746* (2013.01); *G07C 9/00119* (2013.01); *G08B 21/0453* (2013.01); *G08B 25/006* (2013.01); *H04L 67/125* (2013.01)

(58) Field of Classification Search
CPC ..... A61B 5/002; A61B 5/02055; A61B 5/021; A61B 5/024; A61B 5/14551; A61B 5/746; G06F 19/3418
See application file for complete search history.

(56) References Cited

U.S. PATENT DOCUMENTS

| | | | |
|---|---|---|---|
| 2014/0142963 A1* | 5/2014 | Hill .................. | G06F 19/3418 705/2 |
| 2016/0005300 A1* | 1/2016 | Laufer ............... | H04W 4/02 340/573.1 |
| 2016/0292373 A1* | 10/2016 | Spors ............... | G06Q 10/0633 |

* cited by examiner

*Primary Examiner* — Curtis Odom
(74) *Attorney, Agent, or Firm* — Seager Tufte & Wickhem, LLP

(57) ABSTRACT

A system and approach for integrating of health parameters from wearable cloud connected access control devices to provide life safety measures, and also for controlling access to facilities. A monitoring system may incorporate a device for a wearer or holder and a sensor at an entrance to or exit from a specified facility, and a processor connected to the sensor. The device may sense a parameter of the wearer or holder selected from a group of items incorporating heartbeat, blood pressure, blood oxygen, pulse rate, and body temperature. If the selected parameter indicates an abnormal or worsening condition, then the wearer or holder may obtain access to a hospital or health care facility. Health professionals may hold or wear a device that permits them to enter a restricted facility to aid a person within the facility needing medical assistance.

18 Claims, 4 Drawing Sheets

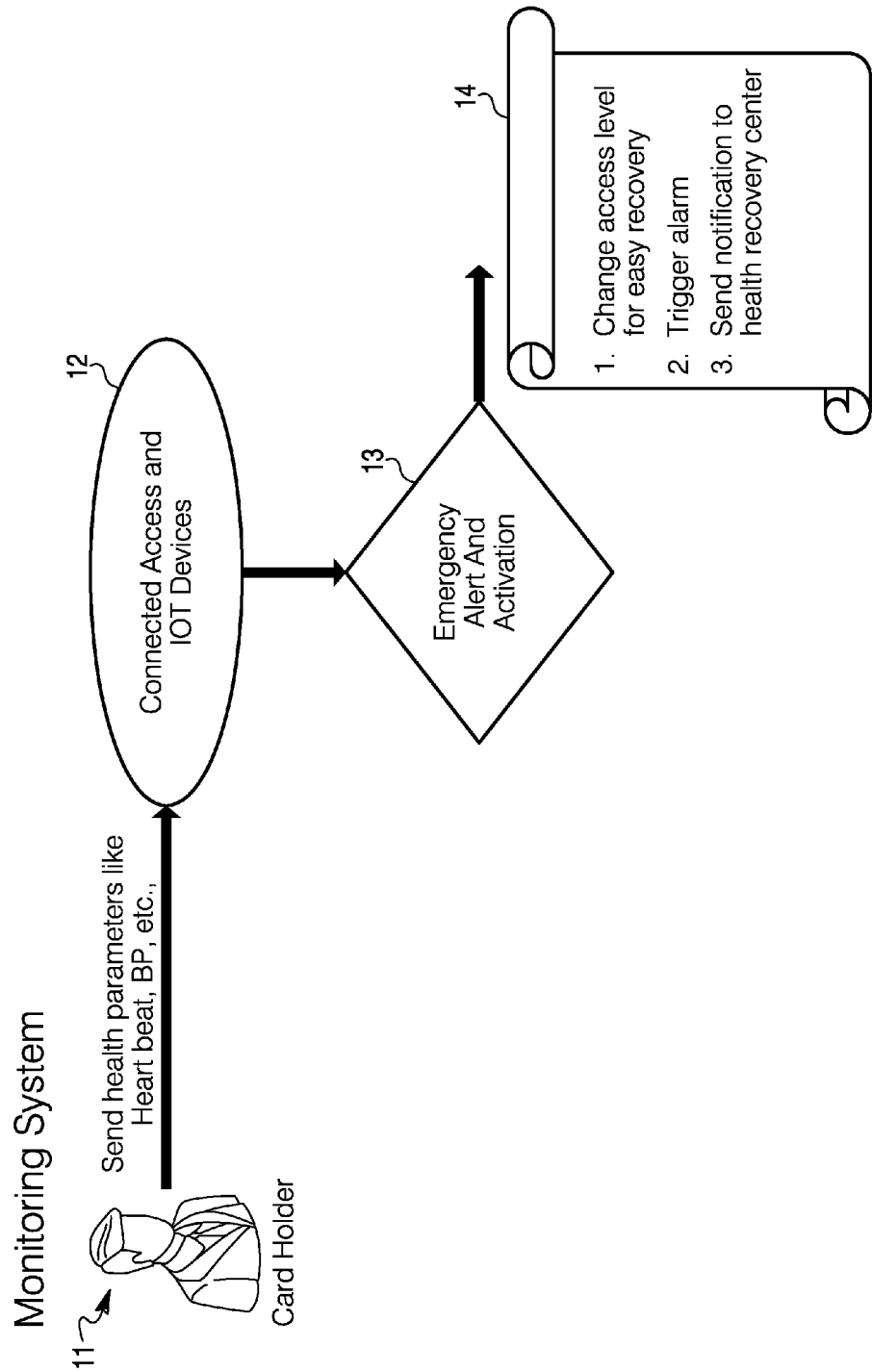

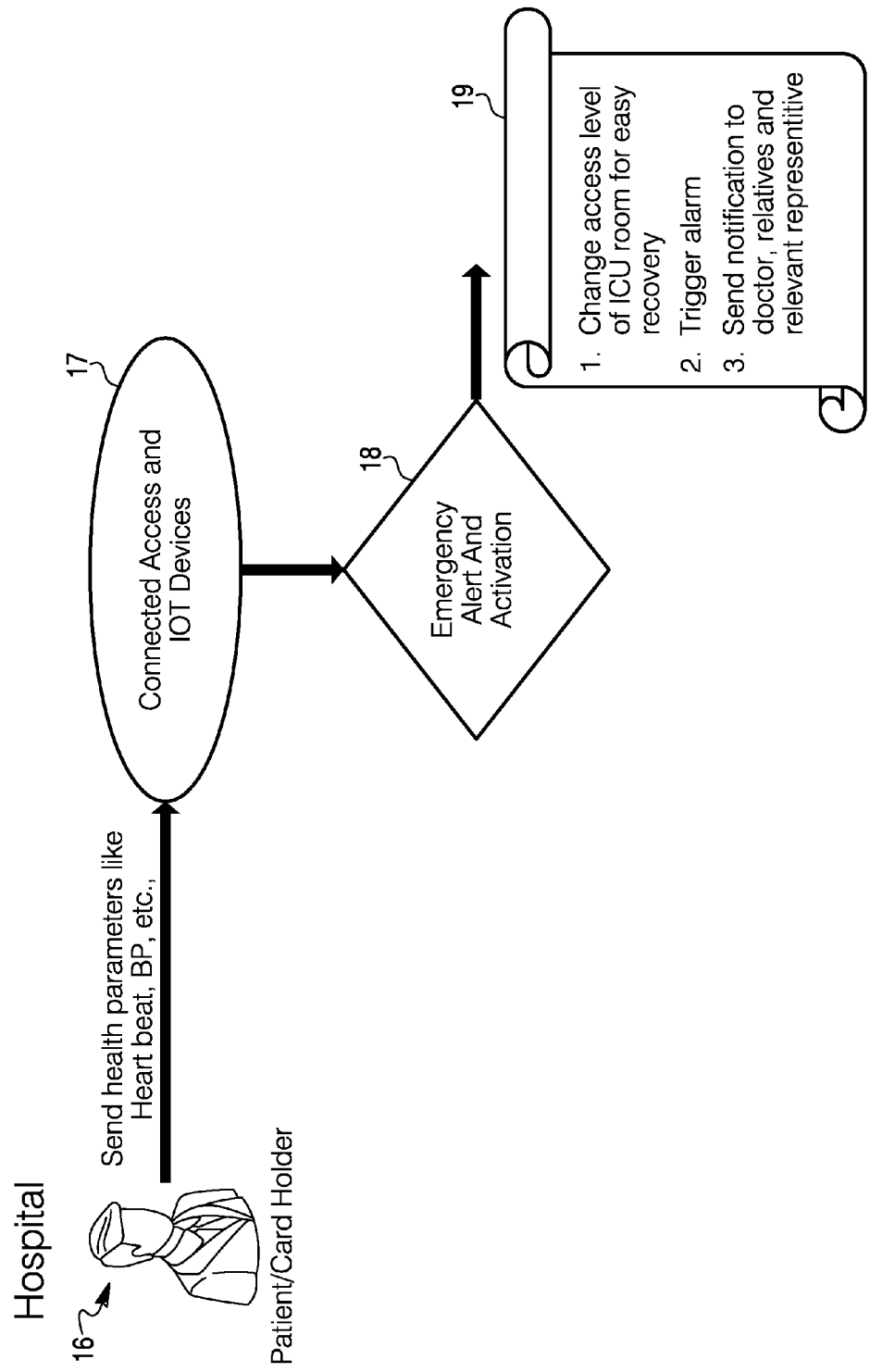

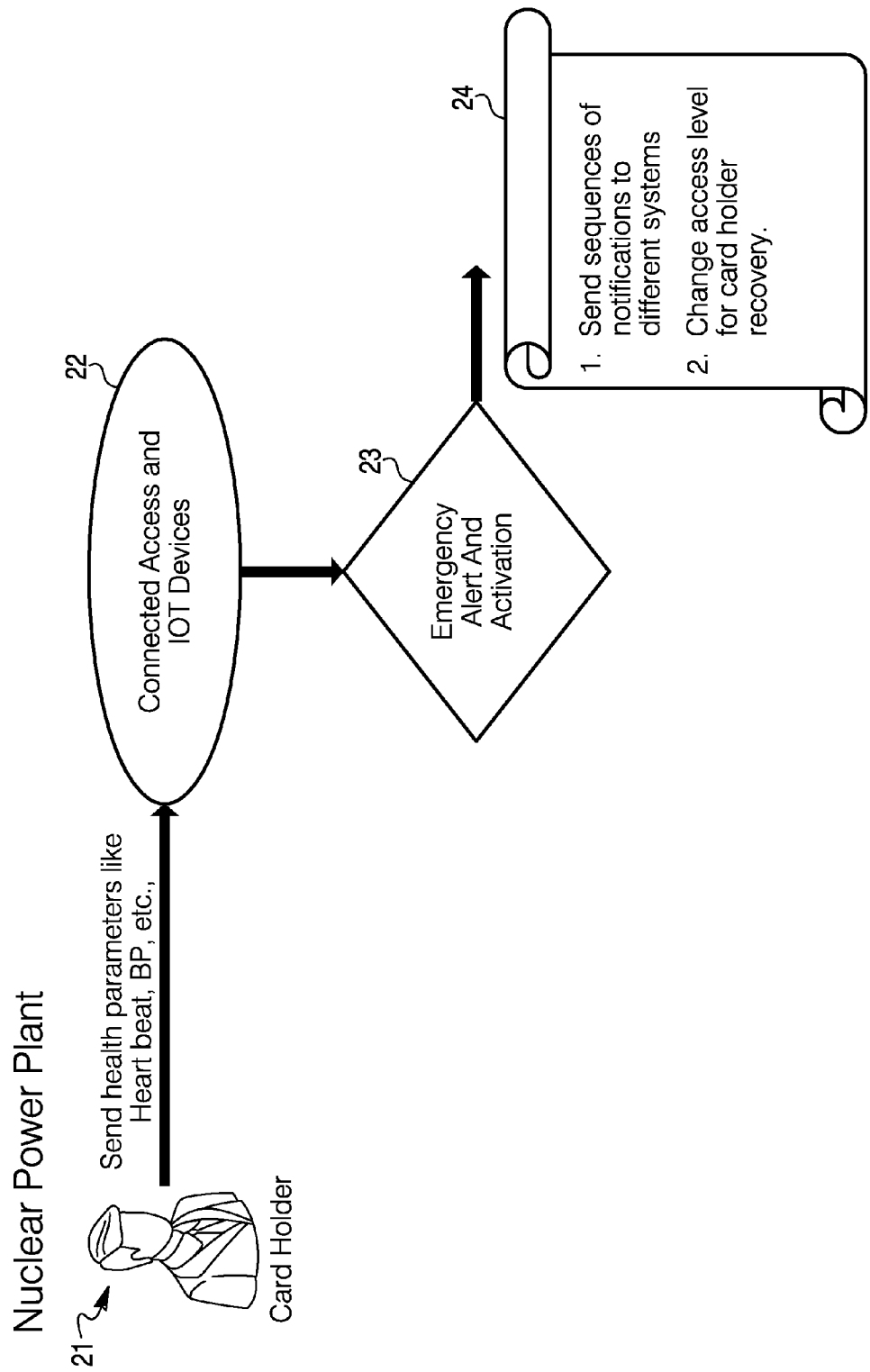

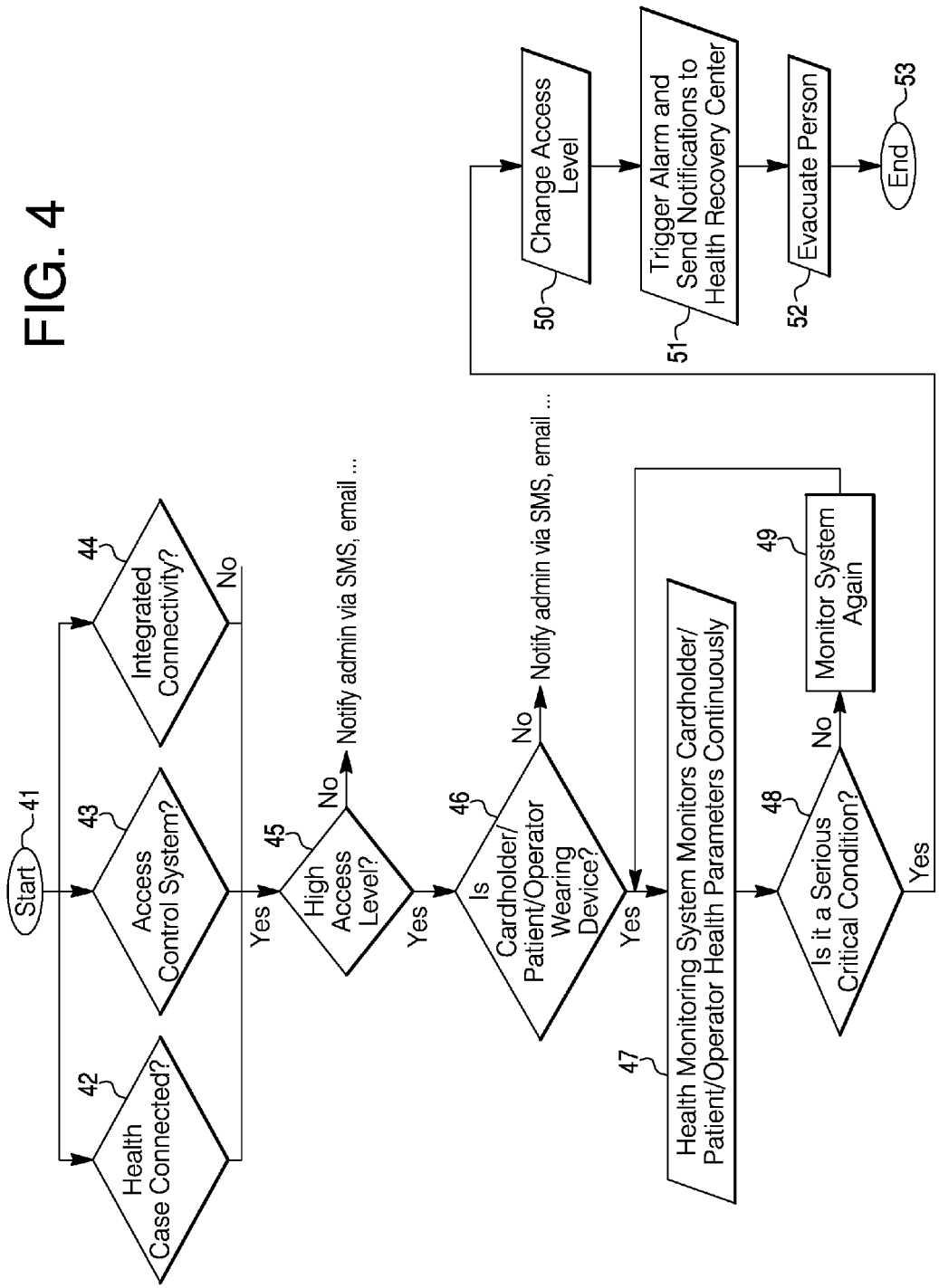

SYSTEM AND APPROACH FOR INTEGRATION OF PARAMETERS FROM WEARABLE CLOUD CONNECTED ACCESS CONTROL DEVICES

BACKGROUND

The present disclosure pertains to health monitors and particularly to health alert systems.

SUMMARY

The disclosure reveals an illustrative example of a system and approach for integrating of health parameters from wearable cloud connected access control devices to provide life safety measures, and also for controlling access to facilities. A monitoring system may incorporate a device for a wearer or holder and a sensor at an entrance to or exit from a specified facility, and a processor connected to the sensor. The wearer or holder with the device may enter or leave the specified facility. The sensor may read the device if the device is within a predetermined distance from the sensor. Signals from the sensor read from the device may go to the processor which determines from the signals whether the wearer or holder is allowed to enter or leave the specified facility. If the wearer or holder with the device is leaving the facility, a message from an indicator or speaker at the sensor location may remind the wearer or holder that a particular action should be performed within the facility prior to a departure. If the wearer or holder with the card attempts to enter the facility, the wearer or holder may enter the facility if the sensor reads certain signals from the card. The device may sense a parameter of the wearer or holder selected from a group of items incorporating heartbeat, blood pressure, blood oxygen, pulse rate, and body temperature. If the selected parameter indicates an abnormal condition of the wearer or holder, the wearer or holder may obtain access to a hospital or health care facility. The device may make an internet connection and transmit signals to the processor at the specified facility. The wearer or holder may monitor the parameter from the device. The parameter may be monitored from a special website designed for monitoring the parameter and health situations related to the parameter. A panel may receive the parameter from the device. If the parameter worsens, then the panel may automatically trigger an alarm to an administrator so that the administrator knows that the wearer or holder needs help, or an access level is modified for entrance of the wearer or holder to a hospital or health facility. Health professionals may hold or wear a device that permits them to enter a restricted facility to aid a person within the facility needing medical assistance.

BRIEF DESCRIPTION OF THE DRAWING

FIG. 1 is a diagram of a health monitoring system layout;

FIG. 2 is a diagram of a health monitoring and alerting scheme for a hospital or a health clinic;

FIG. 3 is a diagram of a health monitoring and alert system layout for a nuclear power plant or like facility; and FIG. 4 is a diagram for an integration of health parameters from wearable cloud connected monitor and access control devices to provide improved life safety services.

DESCRIPTION

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

A high level of secured areas like nuclear power plants, building monitoring room, control room, ICU room in a hospital where only restricted and high secure access level may be provided to, for example, card holders or item or device wearers. In a hospital intensive care unit scenario, very few people such as a doctor and nurses may be allowed to enter a room. In nuclear power plants, scientists and high profile security personnel may be allowed and also a few monitoring stations, with very few operators may be allowed. If there is any medical emergency support required for people inside the premises, they should raise an alarm and only those people who are having access to the room may enter the premises and save the people.

An emergency notification system should trigger manually in the scenarios which have been integrated with access control panels, so that notification and counter action for the notification may be taken. Sometimes, a victim card holder will not necessarily be in a position to trigger an alarm because of a critical emergency health condition. In this scenario, nobody will necessarily be there to help and save the victim card holder. This scenario may lead to life threatening situations to the card holder.

In a present technology evolution the aforesaid issue may be solved by cloud deployment with an integration of wearable and internet of things (IOT) of access and security devices. The critical card holder may have to wear the wearable item which can keep on track the health parameters like blood pressure, heart beat and other parameters based on the site deployment.

In a case of a hospital, a patient's different magnitudes of a health parameter may be sent to connected access devices. If any critical emergency occurs, the system should take a decision based on configure rules, something like changing the access levels so that the doors for aid can be accessed easily.

In case of a building monitoring station, the card holder having a questionable health parameter may be sent to connected access devices. If any critical emergency occurs, the system may make a decision based on a configured rule, something like changing the access levels so that, the doors for aid can be accessed easily. Also the system may alert any connected communication devices to arrange a recovery process from a hospital.

In a case of building nuclear stations, an employee's or scientist's health parameter may be sent to connected access devices. If any critical emergency occurs, the system may make a decision based on the configured rule, something like changing the access levels so that, the doors for aid can be accessed easily. Also the system may alert any connected communication devices to arrange a recovery process with or from a hospital. The system may also initiate a sequence of actions based on the configured rule.

Wearable health monitoring devices may provide health parameters like heartbeat, blood pressure, pulse rate, and so on, and be connected to the web in various ways. Some devices may enable wearers to monitor their own body parameter readings using a mobile phone and a special website designed for monitoring parameters and health situations.

A panel may store data of each card holder and every time there is a change in the condition of the card holder, the data may be refreshed. The panel may receive heart beat rate, blood pressure from wearable health monitor devices as digital data periodically. If any one of the card holder conditions worsens (e.g., heartbeat goes below the "normal" rate), the panel may automatically trigger an alarm, so the administrator knows that the cardholder, such as an employee, needs help and that an access level can be modified accordingly for safer evacuation of the card holder to a hospital.

FIG. 1 is a diagram of a health monitoring system layout. A card holder 11 may send information, such as health parameters like heart beat, blood pressure, breathing rate, oxygen content in blood, and so forth, to a connected access and internet of things (IOT) devices at symbol 12. Information from items of symbol 12 may go to symbol 13 for emergency alert and activation as needed. Such emergency alert and activation may result in actions, some of which are listed in symbol 14. They may incorporate change of access level for easy recovery, trigger alarms, and notification sent to a health recovery center.

FIG. 2 is a diagram of a hospital or a health clinic layout. A patient and/or cardholder 16 may send information, such as health parameters like heart beat, blood pressure, breathing rate, oxygen content in blood, and so forth, to a connected access and IOT devices 17. Information from items indicated by symbol 17 may go to a symbol 18 for emergency alert and activation as needed. Such emergency alert and activation may result in actions, some of which are listed in symbol 19. The actions may incorporate change of access level of intensive care unit (ICU) room for easy recovery, trigger alarm, and send a notification to a doctor, relatives and a relevant representative.

FIG. 3 is a diagram of a health monitoring and alert system layout for a nuclear power plant or like facility. A card holder 21 may send information, such as health parameters like heartbeat, blood pressure, breathing rate, oxygen content in blood, and so forth, to a connected assess and IOT devices at symbol 22. Information from items indicated by symbol 22 may go to a symbol 23 for emergency alert and activation as needed. Such emergency alert and activation may result in action, some of which are listed in symbol 24. The actions may incorporate send sequences of notifications to different systems and change access level for card holder recovery.

FIG. 4 is a flow diagram for an integration of health parameters from wearable cloud connected monitor and access control devices to provide improved life safety services. From a start 41, questions of whether a situation is health case connected, whether there is an access control system, and whether there is integrated connectivity may be asked at symbols 42, 43 and 44, respectively. If an answer is yes to any one or more of the questions, then a question of whether there is a high access level may be asked at symbol 45. If the answer is no for all of the questions at symbols 42-44, then an administration may be notified via SMS, email, or the like. If the answer is yes, then a question at symbol 46 may be asked as to whether a cardholder, patient, operator or other person to be monitored, is wearing a monitoring device. If an answer is no, then the administration may be notified via SMS, email, or the like. If the answer is yes, the a health monitoring system may monitor the cardholder, patient, operator or other person, relative to health parameters continuously at symbol 47. A question of whether there is a serious/critical condition may be asked at symbol 48. If an answer is no, then the system may be monitored again as indicated at symbol 49, where a return is made to symbol 47. If the answer is yes at symbol 48, then an access level may be changed as indicated at symbol 50. An alarm may be triggered and one or more notifications may be sent to a health recovery center as indicated at symbol 51. A person with the serious or critical condition may be evacuated to a health facility for care according to symbol 52, and an end of the present flow of activity may be occur at symbol 53.

To recap, a monitoring system may incorporate a device for a holder, a sensor that detects information on the device at an entrance to or exit from a specified facility having limited access, and a processor connected to the sensor. Detected information on the device may permit the holder to enter or leave the specified facility. The sensor may read the device if the device is within a predetermined distance from the sensor. Signals from the sensor read from the device may go to the processor which determines from the signals whether the device holder is allowed to enter or leave the specified facility. The device may monitor one or more health parameters of the holder.

The device may sense a parameter of the holder selected from a group incorporating heartbeat, blood pressure, blood oxygen, pulse rate, and body temperature. If the selected parameter indicates an abnormal condition of the holder, the holder may obtain access to a health care facility.

The device may make an internet connection and transmit signals to the processor at the specified facility.

The holder may monitor the parameter from the device.

The parameter may be monitored from a special website designed for monitoring the parameter and health situations related to the parameter.

A panel may receive the parameter from the device. If the parameter worsens, then the panel may automatically trigger an alarm to a health administrator so that the health administrator knows that the holder needs help, or an access level is modified for entrance of the holder to a hospital.

If the holder with the device is leaving the facility, a message from a speaker or indicator at the sensor location may remind the holder that a particular action should be performed within the facility prior to a departure.

If the device holder with the device attempts to enter the facility, the holder may enter the facility only if the sensor reads certain signals from the device.

An approach for health monitoring, may incorporate sensing one or more health parameters with a card about a person holding a card, sending the one or more health parameters from the card to one or more IOT (internet of things) devices, evaluating the one or more health parameters with the one or more IOT devices, and initiating an emergency alert and activation as necessary in response to the evaluating of the one or more health parameters.

The approach may further incorporate sending sequences of notifications to various health recovery facilities, and changing an access level as needed for entry, by the person holding the card, to a health recovery facility.

The approach may further incorporate triggering an alarm relative to the emergency alert, changing an access level of the person holding the card as necessary for entry to a health recovery facility, sending a notification to the health recovery facility, and sending a notification to a doctor, representatives, relatives and other entities of the person.

The approach may further incorporate sending sequences of notifications to various sections of a non-medical facility, and setting an access level needed for entry to a health recovery facility inside or outside of the non-medical facility.

The approach may further incorporate setting access levels for medical personal to enable them to enter a non-medical facility to assist in health recovery of the person holding the card.

The approach may further incorporate basing the evaluating the one or more health parameters with the one or more IOT devices on a configuration rule.

An access control mechanism may incorporate a wearable item, a first internet interface connected to the wearable item, a cloud, and a second internet interface connected to an access control panel at one or more facilities and the cloud. The wearable item may be on a person. The wearable item may provide information about the person to the cloud via the first internet interface. The one or more facilities may obtain the information about the person from the cloud via the second internet interface.

The access control panel may determine an access level for the person to the one or more facilities based at least in part on the information about the person.

A first access level may be the highest level for access to the one or more facilities. A third access level may the lowest level for access to the one or more facilities. A second access level may be between the lowest level and the highest level for access to the one or more facilities. At least one of the one or more facilities may be a medical facility. An access level for a medical person assigned to the medical facility may be at a first access level. The access level for a person that has a health condition determined by one or more abnormal readings of parameters sensed by the wearable item on the person, may be changed from a third access level to a second access level.

If the access level for the person is changed to the second access level, then one or more persons or agencies for notification may be selected from a group incorporating nearest of kin, ambulance service, supervisor of the person, and medical services.

Decisions may be based on a configured rule that considers items of information about the person selected from a group consisting of levels of access, parameters sensed by the wearable item, destinations for aid, recovery processes, urgency of care needed, and evacuation.

At least one of the one or more facilities may be selected from a group incorporating high security facilities, facilities holding valuable items, dangerous facilities, and monitoring facilities. The access level of a person that is assigned to the high security facility may be at the first access level. The access level for a person that is not authorized to be at the facility may be the third access level. The access level for a person that is guest at the facility may be a second access level. The second access level may be between the first access level and the third access level. The second access level may be changed for a person in view of new information about the person or the facility.

Information from the wearable item may indicate, at least in part, what access level that the person with the wearable item is granted.

Any publication or patent document noted herein is hereby incorporated by reference to the same extent as if each publication or patent document was specifically and individually indicated to be incorporated by reference.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A monitoring system comprising:
a device for a holder;
a sensor that detects information on the device at an entrance to or exit from a specified facility having limited access; and
a processor connected to the sensor; and
wherein:
detected information on the device permits the holder to enter or leave the specified facility;
the sensor reads the device if the device is within a predetermined distance from the sensor;
signals from the sensor read from the device go to the processor which determines from the signals whether the device holder is allowed to enter or leave the specified facility; and
the device monitors one or more health parameters of the holder.

2. The system of claim 1, wherein:
the device senses a parameter of the holder selected from a group comprising heartbeat, blood pressure, blood oxygen, pulse rate, and body temperature; and
if the selected parameter indicates an abnormal condition of the holder, the holder can obtain access to a health care facility.

3. The system of claim 2, wherein the device makes an internet connection and transmits signals to the processor at the specified facility.

4. The system of claim 2, wherein the holder can monitor the parameter from the device.

5. The system of claim 4, wherein the parameter can be monitored from a special website designed for monitoring the parameter and health situations related to the parameter.

6. The system of claim 3, wherein:
a panel receives the parameter from the device; and
if the parameter worsens, then the panel automatically triggers an alarm to a health administrator so that the health administrator knows that the holder needs help, or an access level is modified for entrance of the holder to a hospital.

7. The system of claim 1, wherein if the holder with the device is leaving the facility, a message from a speaker or indicator at the sensor location can remind the holder that a particular action should be performed within the facility prior to a departure.

8. The system of claim 1, wherein if the device holder with the device attempts to enter the facility, the holder can enter the facility only if the sensor reads certain signals from the device.

9. A method for health monitoring, comprising:
sensing one or more health parameters with a card about a person holding a card;
sending the one or more health parameters from the card to one or more IOT (internet of things) devices;
evaluating the one or more health parameters with the one or more IOT devices;
initiating an emergency alert and activation as necessary in response to the evaluating of the one or more health parameters; and
setting access levels for medical personnel to enable them to enter a non-medical facility to assist in health recovery of the person holding the card.

10. The method of claim 9, further comprising:
sending sequences of notifications to various health recovery facilities; and
changing an access level as needed for entry, by the person holding the card, to a health recovery facility.

11. The method of claim 9, further comprising:
triggering an alarm relative to the emergency alert;
changing an access level of the person holding the card as necessary for entry to a health recovery facility;
sending a notification to the health recovery facility; and
sending a notification to a doctor, representatives, relatives and other entities of the person.

12. The method of claim 9, further comprising:
sending sequences of notifications to various sections of a non-medical facility; and
setting an access level needed for entry to a health recovery facility inside or outside of the non-medical facility.

13. The method of claim 9, further comprising basing the evaluating the one or more health parameters with the one or more IOT devices on a configuration rule.

14. An access control mechanism comprising:
a wearable item;
a first internet interface connected to the wearable item;
a cloud; and
a second internet interface connected to an access control panel at one or more facilities and the cloud; and
wherein:
the wearable item is on a person;
the wearable item provides information about the person to the cloud via the first internet interface; and
the one or more facilities obtain the information about the person from the cloud via the second internet interface;
wherein:
a first access level is the highest level for access to the one or more facilities;
a third access level is the lowest level for access to the one or more facilities;
a second access level is between the lowest level and the highest level for access to the one or more facilities;
at least one of the one or more facilities is a medical facility;
an access level for a medical person assigned to the medical facility is at a first access level; and
the access level for a person that has a health condition determined by one or more abnormal readings of parameters sensed by the wearable item on the person, is changed from a third access level to a second access level.

15. The mechanism of claim 14, wherein the access control panel determines an access level for the person to the one or more facilities based at least in part on the information about the person.

16. The mechanism of claim 14, wherein if the access level for the person is changed to the second access level, then one or more persons or agencies for notification are selected from a group comprising nearest of kin, ambulance service, supervisor of the person, and medical services.

17. The mechanism of claim 14, wherein decisions are based on a configured rule that considers items of information about the person selected from a group comprising of levels of access, parameters sensed by the wearable item, destinations for aid, recovery processes, urgency of care needed, and evacuation.

18. The mechanism of claim 15, wherein:
at least one of the one or more facilities is selected from a group comprising high security facilities, facilities holding valuable items, dangerous facilities, and monitoring facilities;
the access level of a person that is assigned to the high security facility is at the first access level;
the access level for a person that is not authorized to be at the facility is the third access level;
the access level for a person that is guest at the facility is a second access level;
the second access level is between the first access level and the third access level;
the second access level can be changed for a person in view of new information about the person or the facility; and
information from the wearable item indicates, at least in part, what access level that the person with the wearable item is granted.

* * * * *